United States Patent [19]

Weuste et al.

[11] Patent Number: 5,596,125
[45] Date of Patent: Jan. 21, 1997

[54] PROCESS FOR THE PREPARATION OF QUATERNARY DIESTERS

[75] Inventors: Burkhard Weuste, Gummersbach; Hans J. Weissen, Kreuzau; Andrea G. Fischer, Jülich, all of Germany

[73] Assignee: Akzo Nobel nv, Arnhem, Netherlands

[21] Appl. No.: 519,558

[22] Filed: Aug. 25, 1995

[30] Foreign Application Priority Data

Aug. 29, 1994 [EP] European Pat. Off. .............. 94202451

[51] Int. Cl.⁶ .................................................. C07C 229/00
[52] U.S. Cl. ......................... 560/171; 544/171; 546/248
[58] Field of Search ........................... 560/171; 544/171; 546/248

[56] References Cited

FOREIGN PATENT DOCUMENTS 0021431  1/1981  European Pat. Off. .
WO93/25648  12/1993  WIPO .

OTHER PUBLICATIONS

European Search Report dated Jan. 11, 1995.
English Language abstract of EP A 0 021431 (1981).

*Primary Examiner*—Michael L. Shippen
*Attorney, Agent, or Firm*—Ralph J. Mancini; Louis A. Morris

[57] ABSTRACT

The present invention relates to a process for the preparation of quaternary diesters of the formula:

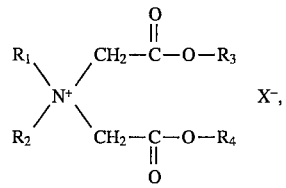

wherein $X^-$ represents a halogen atom, $R_1$ and $R_2$ are the same or different and are selected from an alkyl group having 1 to 3 carbon atoms or a hydroxyethyl group, or may be linked together to form an alkylene group having 4 to 6 carbon atoms which may be interrupted by an N atom or O atom, and $R_3$ and $R_4$ are the same or different and are selected from an alkyl group or alkenyl group having 8 to 22 carbon atoms, or may be linked together to form an alk-(en)ylene group having 8 to 22 carbon atoms. In the process a) a secondary amine of the formula $R_1$—NH—$R_2$ is gradually added to and converted with one or more liquid compounds of the formula

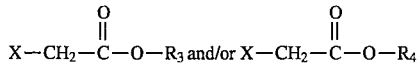

a molar ratio in the range of 1.0:1.0 and 1.0:1.2, after which b) the formed solid amine hydrohalide is separated followed by c) an aftertreatment, optionally in a solvent, at elevated temperature until the conversion is substantially complete, after which, if so desired, further treatments, such as recrystallization from an organic solvent, are carried out to achieve a special product form.

12 Claims, No Drawings

PROCESS FOR THE PREPARATION OF QUATERNARY DIESTERS

FIELD OF THE INVENTION

The present invention generally relates to a process for the preparation of quaternary ammonium diesters.

BACKGROUND OF THE INVENTION

A process for the preparation of quaternary diesters is disclosed by EP-A-21 431. A drawback to the known process described in this document is that it is a comparatively elaborate two-step process, with a secondary amine of the formula $R_1$—NH—$R_2$ being converted by addition thereto of an equimolar amount of monochloroacetate ester in the first step, followed by separation of the formed reaction product and addition of a further equivalent amount of monochloroacetate ester in a second step.

The present invention overcomes the deficiencies of the prior art and provides a highly simplified, one-step process for the preparation of quaternary diesters.

SUMMARY OF THE INVENTION

The invention relates to a process for the preparation of quaternary diesters of the formula:

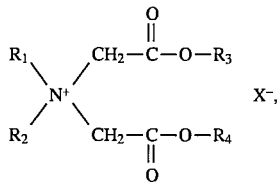

wherein $X^-$ represents a halogen atom, notably a chlorine atom or a bromine atom, $R_1$ and $R_2$ may be the same or different and have the meaning of an alkyl group having 1 to 3 carbon atoms or a hydroxyethyl group, or be linked together to form an alkylene group having 4 to 6 carbon atoms which may be interrupted by an N atom or O atom, and $R_3$ and $R_4$ may be the same or different and have the meaning of an alkyl group or alkenyl group having 8 to 22 carbon atoms, or be linked together to form an alk(en)ylene group having 8 to 22 carbon atoms, by conversion of a secondary amine of the formula $R_1$—NH—$R_2$ with halogen acetate esters of the formulae X—$CH_2$—C(O)—O—$R_3$ and X—$CH_2$—C(O)—O—$R_4$.

DETAILED DESCRIPTION OF THE INVENTION

The invention relates to a process for the preparation of quaternary diesters of the formula:

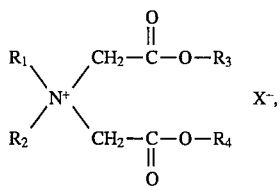

wherein $X^-$ represents a halogen atom, notably a chlorine atom or a bromine atom, $R_1$ and $R_2$ may be the same or different and have the meaning of an alkyl group having 1 to 3 carbon atoms or a hydroxyethyl group, or be linked together to form an alkylene group having 4 to 6 carbon atoms which may be interrupted by an N atom or O atom, and $R_3$ and $R_4$ may be the same or different and have the meaning of an alkyl group or alkenyl group having 8 to 22 carbon atoms, or be linked together to form an alk(en)ylene group having 8 to 22 carbon atoms, by conversion of a secondary amine of the formula $R_1$—NH—$R_2$ with halogen acetate esters of the formulae X—$CH_2$—C(O)—O—$R_3$ and X—$CH_2$—C(O)—O—$R_4$.

More specifically, in the process of the present invention:

a) a secondary amine of the formula $R_1$—NH—$R_2$ is gradually added to and converted with one or more liquid compounds of the formula

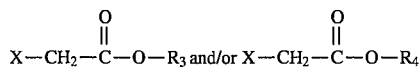

at a molar ratio in the range of 1.0:1.0 and 1.0:1.2, after which b) the formed solid amine hydrohalide is separated, followed by c) an aftertreatment, optionally in a solvent, at elevated temperature until the conversion is virtually complete, after which, if so desired, further treatments, such as recrystallization from an organic solvent, are carried out to achieve a special product form.

It was found that when the now proposed process is used, 0.1 to 10 wt. % of the obtained quaternary ester compounds is made up of a monoester quat. Surprisingly, it was found that this presence, preferably in an percentage of 0.2 to 5 wt. %, has a high viscosity reducing effect on diester quat-containing aqueous dispersions.

It should be noted that in WO 93/25648 the preparation of the quaternary diesters mentioned in the opening paragraph also involves the addition of the secondary amine to a solution of chloroacetate esters. However, the amount of secondary amine added is a multiple of that which is added according to the process of the present invention. In consequence, in the known process only the monoester amine is obtained in the first instance; it takes a second step and a second chloroacetate ester for it to be converted to the corresponding diester.

As secondary amine of the formula $R_1$—NH—$R_2$ may be used symmetrical as well as asymmetrical compounds. Alternatively, mixtures of secondary amines may be employed. Examples of suitable secondary amines include: piperidine, morpholine, methylethyl, dipropyl, hydroxyethylmethyl, and diethyl amine. Preference is given in this case to the use of dimethyl amine. The halogen acetate esters employed may be either chloroacetate esters or bromoacetate esters.

Suitable alcohols for the preparation of the chloro- or bromoacetate esters include branched and linear, saturated and olefinically unsaturated alcohols having 8 to 24 carbon atoms. As examples of the alcohols may be mentioned dodecyl, myristyl, cetyl, oleyl, stearyl, behenyl and/or tallow alcohol. Preference is given in this case to a process in which the secondary amine is dimethyl amine and the halogen acetate esters are tallow chloroacetate esters.

It has been found that the purity of the final product is very much connected with the molar ratio of the secondary amine to the halogen acetate ester. Optimum results were found to be obtained using a process in which the reaction in step a) was carried out at a molar ratio of the secondary amine to the halogen acetate ester(s) in the range of 1.0:1.0 to 1.0:1.05.

The temperature at which the secondary amine is added is generally in the range of 50° to 110° C., preference being given to addition at a temperature in the range of 60° to 100° C. Adding of the secondary amine commonly takes from 15 minutes to 10 hours, preferably from 30 minutes to 5 hours. Depending on the duration of the addition of the secondary amine, the reaction is continued 5 minutes to 3 hours, preferably 10 minutes to 1.5 hours, at a temperature in the range of 50° to 110° C., preferably in the range of 60° to 100° C.

Finally, the amine hydrohalide is separated from the reaction mixture, e.g., by filtration at a temperature in the range of 90° to 100° C.

The aftertreatment generally is carried out at a temperature in the range of 40° to 100° C., preferably in the range of 50° to 80° C. The solvent used in the aftertreatment advantageously is ethanol and/or isopropanol. Any further purification is preferably carried out by recrystallization from a solvent such as methanol, ethanol, propanol, isopropanol, acetone and/or ethyl acetate. The diester quats obtained in this manner display an outstanding combination of superior softening performance, rapid biodegradability, low algae toxicity and low fish toxicity. Furthermore, they are easy to disperse due to the presence of appropriate amounts of monoester quats whose formation is controlled by the process according to the present invention.

The invention will be further illustrated with reference to the following examples nonlimiting.

EXAMPLE I

In a 1 l glass three-necked flask fitted with a stirrer, a heating jacket, and a dropping funnel 504 g of tallow chloroacetate were heated to 80° C. in an atmosphere of nitrogen. 100 ml of dimethyl amine were gradually added over 40 minutes, with care being taken to maintain the reaction temperature of 80° C. Next, the reaction mixture was filtered after heating to 95° C. The filtrate was diluted with 42 g of isopropanol and then subjected to an aftertreatment at 60° C. for 3 hours, whereupon, after evaporation of the solvent, dimethyl ditallowester quat was obtained. The product was then dissolved in 3.6 l of acetone and 150 ml of isopropanol. Obtained were 395 g of a white crystalline product composed of 94.1 wt. % of dimethyl ditallowester quat and 2.1 wt. % of trimethyl monotallowester quat.

EXAMPLE II

The preparation of Example I was repeated up to and including an aftertreatment at 60° C. for 3 hours. Finally, the thus obtained product was adjusted with a further 48 g of isopropanol to obtain an 85 per cent solids product containing 81.7 wt. % of dimethyl ditallowester quat and 3.5 wt. % of trimethyl monotallowester quat (in relation to solids).

EXAMPLE III

The following example shows that the presence of a small quantity of mono-ester quat has a surprisingly major effect on the viscosity of a substantially diester quat-containing aqueous dispersion. The diester quat was made up of the dimethyl ditallowester quat of Example I, hereinafter diester quat A. The monoester quat was made up of the corresponding trimethyl monotallowester quat, hereinafter monoester quat M.

| aqueous dispersion | I | II | III |
|---|---|---|---|
| diester quat A, wt. % | 5.0 | 5.0 | 5.0 |
| monoester quat M, wt. % | 0 | 0.2 | 0.5 |
| viscosity (20° C., mPa.s) | 1280 | 140 | 50 |

We claim:

1. A process for the preparation of quaternary diesters of the formula:

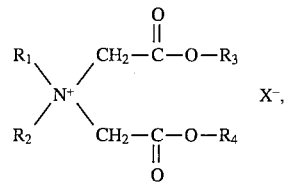

wherein $X^-$ is a halogen, $R_1$ and $R_2$ are the same or different and are selected from an alkyl group having 1 to 3 carbon atoms, a hydroxyethyl group, or may be linked together to form an alkylene group having 4 to 6 carbon atoms which may be interrupted by an N atom or O atom, and $R_3$ and $R_4$ are the same or different and are selected from an alkyl group or alkenyl group having 8 to 22 carbon atoms, or be linked together to form an alk(en)ylene group having 8 to 22 carbon atoms, wherein said process comprises a) gradually adding a secondary amine of the formula $R_1$—NH—$R_2$ to one or more liquid compounds of the formula

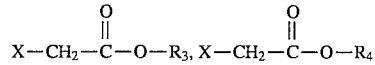

or mixtures thereof at a molar ratio of from about 1.0:1.0 to 1.0:1.2, in order to form solid amine hydrohalide, b) separating the formed solid amine hydrohalide from the reaction mixture, c) and further subjecting said solid amine hydrohalide to an aftertreatment, at elevated temperature, until the conversion is substantially complete, and the quaternary diester product is obtained.

2. The process of claim 1 wherein the reaction in step a) is carried out at a molar ratio of the secondary amine to the halogen acetate ester(s) in the range of from about 1.0:1.0 to 1.0:1.05.

3. The process of claim 1 wherein the secondary amine is added at a temperature in the range of 50° to 110° C.

4. The process of claim 1 wherein the amine hydrohalide is separated by filtration at a temperature in the range of 90° to 100° C.

5. The process of claim 1 wherein the aftertreatment according to step c) is carried out at a temperature of from about 40° to 100° C.

6. The process wherein to claim 1, wherein the solvent employed in the aftertreatment is selected from ethanol, isopropanol, or mixtures thereof.

7. The process of claim 2 wherein said quaternary diester product is further purified by recrystallizing same from an organic solvent.

8. The process of claim 7 wherein the solvent employed in the recrystallization is methanol, ethanol, propanol, isopropanol, acetone, ethyl acetate, or mixtures thereof.

9. The process of claim 3 wherein the secondary amine is added at a temperature of from about 60° to 100° C.

10. The process of claim 5 wherein said aftertreatment of step C) is conducted at a temperature of from about 40° to 100° C.

11. The process of claim 1 wherein $X^-$ is chlorine or bromine.

12. The process of claim 1 wherein said aftertreatment is conducted in a solvent.

* * * * *